(12) United States Patent
Dakka et al.

(10) Patent No.: US 7,420,096 B2
(45) Date of Patent: *Sep. 2, 2008

(54) OLEFIN OLIGOMERIZATION

(75) Inventors: Jihad Mohammed Dakka, Whitehouse Station, NJ (US); Georges M. K. Mathys, Bierbeek (BE); Marc P. H. Puttemans, Dilbeek (BE)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/820,135

(22) Filed: Jun. 18, 2007

(65) Prior Publication Data

US 2007/0260020 A1 Nov. 8, 2007

Related U.S. Application Data

(62) Division of application No. 10/492,706, filed as application No. PCT/GB02/04771 on Oct. 23, 2002, now Pat. No. 7,247,763.

(30) Foreign Application Priority Data

Oct. 24, 2001 (EP) ................... 01309032

(51) Int. Cl.
  *C07C 2/08* (2006.01)
  *C07C 2/02* (2006.01)

(52) U.S. Cl. ............... 585/329; 585/324; 585/502; 585/520; 585/533; 585/518

(58) Field of Classification Search ............... 585/502, 585/520, 533, 324, 329, 518
See application file for complete search history.

(56) References Cited

U.S. PATENT DOCUMENTS

| 2,778,859 | A | 1/1957 | Johnson et al. |
| 4,098,684 | A | 7/1978 | Innes |
| 4,390,413 | A | 6/1983 | O'Rear et al. |
| 4,556,477 | A | 12/1985 | Dwyer |
| 4,973,870 | A | 11/1990 | Uehara |
| 5,167,797 | A | 12/1992 | Ou |
| 5,324,420 | A | 6/1994 | De Munck et al. |
| 5,965,104 | A | 10/1999 | Lee et al. |
| 5,994,601 | A | 11/1999 | Nierlich et al. |
| 6,492,568 | B1 | 12/2002 | Murray et al. |
| 6,566,565 | B1 | 5/2003 | Murray et al. |
| 6,653,514 | B1 | 11/2003 | Murray et al. |
| 7,012,167 | B2 | 3/2006 | Kahn |
| 7,247,763 | B2 * | 7/2007 | Dakka et al. ............ 585/533 |

FOREIGN PATENT DOCUMENTS

| EP | 0 174 121 | 2/1992 |
| EP | 0 746 538 | 1/1999 |
| WO | WO 93/16020 | 8/1993 |
| WO | WO 93/25475 | 12/1993 |
| WO | WO 94/12452 | 6/1994 |
| WO | WO 95/22516 | 8/1995 |
| WO | WO 2005/058782 | 6/2005 |

* cited by examiner

*Primary Examiner*—Glenn Caldarola
*Assistant Examiner*—In Suk Bullock
(74) *Attorney, Agent, or Firm*—Andrew B. Griffis

(57) ABSTRACT

Limiting the sulphur level in olefin feedstocks to zeolite-catalysed oligomerization enhances selectivity to trimer and catalyst life and activity.

9 Claims, No Drawings

OLEFIN OLIGOMERIZATION

This a divisional of application Ser. No. 10/492,706 which is a national stage application of PCT/GB02/04771, filed Oct. 23, 2002 now U.S. Pat. No. 7,247,763.

This invention relates to a process for the manufacture of higher molecular weight organic molecules from lower molecular weight materials, especially olefins, by oligomerization, to crystalline molecular sieves suitable for use in the process, and the use of such molecular sieves in such reactions. The invention also relates to the oligomers produced and their use as feedstocks for further reactions.

Molecular sieve catalysts of many types have been proposed for use in numerous chemical processes. Among such processes are the conversion by oligomerization of lower olefins, e.g., alkenes, to higher olefins, e.g., higher alkenes, for example the oligomerization of $C_2$ to $C_6$, especially $C_3$ and $C_4$, olefins to olefins in the $C_6$ to $C_{12}$ range, and occasionally higher.

An example of the use of crystalline molecular sieves as catalysts for this purpose is given in EP-B-625 132, which describes the advantage of using in zeolite-catalysed olefin oligomerization, a hydrated feedstock, in particular one containing 0.05 to 0.25 molar percent of water. Another example is given in EP-B-746 538, where zeolites of the structure types MFI, TON, and MFS, in their acid forms, are used in oligomerization of propene and butene, the particular members of those structure type families used being ZSM-5, ZSM-22, and ZSM-57. This patent is concerned with controlling the extent of oligomerization, to obtain the desired proportions of or selectivity to dimer, trimer, and higher oligomers, for use in downstream manufacturing processes. In the patent, methods of improving trimer yield are described.

Commercially available feedstocks have been found, however, to cause deactivation of the oligomerization catalyst, and to give a lower selectivity to trimer than might be expected from the disclosure of EP-B-746 538. Although the effects on activity can be countered to some extent by raising the reaction temperature, the catalyst life is reduced by this expedient.

The present invention is based on the observation that high levels of sulphur compounds in the feed appear to be responsible for the problems with commercial feedstocks.

The invention accordingly provides a process for the oligomerization of an olefinic feedstock, which comprises contacting under oligomerization conditions an olefinic feedstock containing from 0.1 to 2 ppm of sulphur-containing compounds by volume with a catalyst comprising a crystalline molecular sieve and recovering a product comprising at least one olefin oligomer.

More especially, the invention comprises reducing the content of sulphur-containing compounds of an olefinic feedstock containing more than 2 ppm by volume thereof to a level of from 0.1 to 2 ppm, before carrying out the oligomerization process.

Advantageously, the sulphur compound content of the feedstock is or is reduced to from 0.2 to 1 ppm by weight.

It has been found that certain types of sulphur-containing compounds are especially deleterious. These are primarily saturated aliphatic compounds, for example the thiols, sulphides, including cyclic sulphides, and disulphides. The low molecular weight materials are especially troublesome, for example dimethyl, diethyl, and ethyl methyl sulphides, n-propane thiol, 1-butane thiol and 1,1-methylethyl thiol, ethylmethyl and dimethyl disulphides, and tetrahydrothiophene. There may also be a steric factor, since n-propyl sulphide is more troublesome than is di-isopropyl sulphide or isopropyl thiol. Aromatic compounds are less troublesome, as is carbonyl sulphide.

It has been found that sulphur compounds adsorbed or absorbed by, but not readily desorbed thermally from, the catalyst are the most troublesome.

Accordingly, the invention also provides a process for the oligomerization of an olefinic feedstock, which comprises contacting under oligomerization conditions an olefinic feedstock containing from 0.1 to 2 ppm, advantageously from 0.2 to 1 ppm, by volume of sulphur-containing compounds having a desorption temperature above 170° C. with a catalyst comprising a crystalline molecular sieve and recovering a product containing at least one olefin oligomer.

More especially the invention provides reducing the sulphur compound content of such a feedstock represented by such compounds to a level of from 0.1 to 2 ppm, advantageously 0.2 to 1 ppm, by volume, before carrying out the process.

The sulphur-containing compound content of a feedstock is conveniently ascertained by gas chromatographic analysis using peak areas normalized with reference to a COS standard.

The crystalline molecular sieve is advantageously of the structure type TON or MFS, the term "structure type" being used in the sense described in the Structure Type Atlas, Zeolites 17, 1996. Examples of TON structure type zeolites include ZSM-22, ISI-1, Theta-1, Nu-10, and KZ-2, and of MFS include ZSM-57, all in their H— or acid form.

The crystalline molecular sieve is advantageously ZSM-22 or, preferably, ZSM-57. ZSM-22 and its manufacture are described in, for example, U.S. Pat. No. 4,556,477 and WO 93/25475, and ZSM-57 and its manufacture in EP-A-174 121 and U.S. Pat. No. 4,973,870, the disclosures of all of which are incorporated herein by reference. Mixtures of two or more molecular sieves may be used, e.g., a mixture of ZSM-22 and ZSM-57.

Although ZSM-22 and ZSM-57 are presently preferred, there may also be used a crystalline molecular sieve of the MTT structure type, exemplified by ZSM-23, EU-13, ISI-4 and KZ-1.

A molecular sieve crystallite size advantageously up to 5 μm, preferably within the range of from 0.05 to 5 μm, more especially from 0.05 to 2 μm, and most preferably from 0.1 to 1 μm, may be employed. The molecular sieve may be supported or unsupported, for example in powder form, or used as an extrudate with an appropriate binder. An as-synthesized molecular sieve is advantageously converted to its acid form by acid treatment, e.g., by HCl, or by ammonium ion exchange, and subsequent calcination before use in the process of the invention. The calcined materials may be post-treated as by steaming. Although the invention will be described with reference to zeolites proper, it is possible to use, as is known in the art, a material in which silicon and aluminium have been replaced in whole or in part by other elements, silicon more especially by germanium and aluminium more especially by boron, gallium, chromium and iron, materials containing such replacement lattice elements also being termed zeolites, and the term is used in the broader sense in this specification, to include aluminophosphates and silico-aluminophosphates (AlPO's and SAPO's).

The olefin feedstock advantageously contains olefins having from 2 to 12 carbon atoms, preferably from 2 to 6 carbon atoms, and is advantageously an alkene-containing feedstock. The feed preferably contains propene, butenes and/or pentenes; the invention is especially applicable to propene oligomerization.

Sulphur-containing compounds may be removed from the feedstream by any method, many of which are used in industry or described in the literature. As examples, there may be mentioned washing the feed with a heavy hydrocarbon, e.g., Isopar L, contacting the feedstream with chloramine-T, as described in U.S. Pat. No. 5,167,797, or use of a guard bed, to absorb sulphur either physically, with for example a molecular sieve, e.g., Z10-08 (trade mark) from Zeochem, or chemically, using a nickel catalyst. Substantially complete sulphur absorption was achieved at 190° C. using a nickel catalyst.

Reaction conditions for the process of the invention may be, with the exception of the presence of the sulphur compound or compounds, in accordance with conditions operative for prior art processes for oligomerization of the same olefin or olefins.

The olefinic feedstock may be fed to the reaction zone in the liquid or, preferably, the supercritical phase. The feedstock may contain water, either present from the feedstock raw material or by addition.

he feedstock advantageously comprises from 0.05 to 0.25, preferably from 0.06 to 0.20 and more preferably from 0.10 to 0.20, molar % water based on the total hydrocarbon content of the feedstock. If desired or required, the natural water content of the feedstock may be increased, for example, by being passed through a thermostatted water saturator. Since the amount of water required to saturate the feedstock will depend upon the temperature and composition of the feedstock, control of the water content may be effected by appropriate control of the temperature of the feedstock.

The feedstock may also comprise an inert diluent, for example, a saturated hydrocarbon. That other hydrocarbon is included in the hydrocarbon content for the purposes of calculation of the water content.

The reaction is advantageously carried out at a temperature within the range of from 130 to 300° C., preferably at a temperature within the range of from 135° to 280° C., more preferably from 160° to 250° C., and most preferably from 160 to 230° C. It will be appreciated that, to maintain desirable conversion rates, it may be advantageous to increase reaction temperatures with the time the catalyst is on stream. Preferably, however, the temperature is kept below 230° C. when possible, to prolong catalyst life.

The pressure is advantageously in the range of 5 to 10 MPa, preferably from 6 to 8 MPa. The olefin hourly space velocity is advantageously in the range of from 0.1 to 20, preferably from 1 to 10, and more preferably from 1.5 to 7.5, $hr^{-1}$.

As indicated above, it was found when using a commercial olefinic feedstock containing more than 2 ppm sulphur-containing compounds by volume, especially a propene-containing feed, that in addition to reduced catalyst activity, the selectivity to trimer on oligomerization was lower than expected from the disclosure of EP-B-746 538. It has been found that by limiting the proportion of sulphur in the feed, selectivity to trimer is improved. Similarly, with limited sulphur in the feed, oligomerization may be performed at lower temperatures, thereby prolonging catalyst life.

The invention accordingly also provides the use of limiting to from 0.1 to 2 ppm, and advantageously from 0.2 to 1 ppm, by volume, the proportion of sulphur-containing compounds in an olefin feedstock being fed to a crystalline molecular sieve catalyst to maintain or enhance (a) selectivity to trimer production or (b) catalyst activity or to maintain or enhance both (a) and (b). Further, since to achieve a given conversion rate with a sulphur-containing feed a higher operating temperature is required, and higher temperatures cause more rapid catalyst ageing, a lower sulphur proportion has a beneficial effect on catalyst lifetime.

The invention accordingly further provides the use of limiting to 0.1 to 2 ppm, and advantageously from 0.2 to 1 ppm, by volume, the proportion of sulphur-containing compounds in an olefin feedstock being fed to a crystalline molecular sieve catalyst to maintain or enhance catalyst life.

The sulphur compounds so limited may be those with a desorption temperature above 170° C.

As indicated above, the oligomers of the invention are especially suitable as feedstocks for further processing, including at least one of the following: fractionation; hydrogenation; hydroformylation; oxidation; carbonylation; etherification; epoxidation, and hydration.

The eventual products may be alcohols, produced for example by hydroformylation and hydrogenation; esters, in which the alcohols are esterified as with inorganic or organic acids, including carboxylic acids, especially polycarboxylic acids; aldehydes, acids, in which the hydroformylation products are oxidized and hydrogenated, and numerous other end uses.

The esters with polycarboxylic acids are especially valuable as plasticizers, and the invention further provides plasticizer compositions comprising the esters, and polymeric compositions especially vinyl chloride polymers, particularly PVC, comprising the esters, and shaped structures formed of the plasticized polymeric compositions.

EXAMPLE

The following examples, in which parts and percentages are by weight unless otherwise indicated, illustrate the invention.

All feeds used in the examples were hydrated by passage through a water saturator at 25 to 40° C. The feeds are as follows:

Feed A—commercial propene feed, containing 48% propene, 3% butenes, 4% ethane, 20% propane, 9% n-butane, 16% isobutane and 22.4 ppm sulphur-containing compounds by volume (3 ppm thiophenes, 2 ppm mercaptans (thiols), 10 ppm dialkyl sulphides, 3 ppm dialkyl disulphides, 1 ppm $H_2S$, the remainder unidentified sulphur-containing species).

Feed B—feed A after sulphur removal by guard bed (sulphur compound content<0.1 ppm by volume).

Feed C—sulphur-free (sulphur compound content <0.1 ppm by volume) propene feed, containing 50% propene, 40% n-butane, 10% isobutane.

Catalyst compositions used are as follows:

Catalyst A—an extruded H-ZSM-57 catalyst
Catalyst B—a powdered sample of H-ZSM-57
Catalyst C—an extruded H-ZSM-22 catalyst.

Olefin monomer conversion rates were derived from gas chromatographic analysis using peak areas normalized to the total sum of the paraffins in the feed as internal standard, conversion being expressed as:

$$\text{conversion \%} = 100 \left[ 1 - \frac{A \ o.m. / A \ \text{paraffins}}{A° \ o.m. / A° \ \text{paraffins}} \right]$$

where A represents chromatographic peak area in product (wt %), A° represents chromatographic peak area in feed (wt %) and o.m. represents olefin monomer(s).

Selectivity to a given oligomer (dimer, trimer, etc.) is also determined from gas chromatographic peak areas, after hydrogenation of the product stream.

Example 1

The specified feeds were passed over catalysts A and B, ZSM-57, at a total feed space velocity of 2 h$^{-1}$, the temperature being increased from 135° C. until an alkene conversion rate of at least 80% is reached. The conversion rate and selectivity to dimer were analysed, and the results are shown in Table 1.

TABLE 1

| Sample | Feed | Jacket Temp ° C. | Catalyst | Conv. % | Nonene Selectivity |
|---|---|---|---|---|---|
| C1 | C | 135 | B | 95 | 74 |
| C2 | C | 165 | A | 95 | 72 |
| 1 | C + 1 ppm CH$_3$SH | 160 | B | 94 | 63 |
| 2 | C + 1 ppm CH$_3$SH | 215 | A | 95 | 63 |
| C3 | C + 7 ppm CH$_3$SH | 228 | A | 96 | 61 |
| C4 | B | 142 | B | 96 | 60* |
| C5 | A | 225 | B | 95 | 53* |

*Selectivity lower than Sample C1 because of co-oligomerization with the butene content of the feed.

The results show that selectivity to nonene is adversely affected by the presence of sulphur-containing compounds.

To various samples of Feed C were added various sulphur compounds before oligomerization over Catalyst B. The initial conversion rate, the decrease in conversion rate with time on stream, and the selectivity to nonenes were observed. The results are shown in Table 2.

We claim:

1. A process for the oligomerization of an olefinic feedstock, which comprises contacting under oligomerization conditions an olefinic feedstock containing from 0.1 to 2 ppm by volume of sulphur-containing compounds having a desorption temperature above 170° C. with a catalyst comprising a crystalline molecular sieve and recovering a product containing at least one olefin oligomer, followed by a step of hydroformylation and hydrogenation, said process further characterized by a step of reducing the content of said sulphur-containing compounds in said feedstock prior to said contacting.

2. The process as claimed in claim 1, wherein said olefinic feedstock contacting said catalyst contains from 0.2 to 1 ppm, by volume of said sulphur-containing compounds.

3. The process as claimed in claim 1, wherein the crystalline molecular sieve is selected from those crystalline molecular sieves having the TON structure, the MFS structure, or a mixture thereof.

4. The process as claimed in claim 1, wherein the crystalline molecular sieve is selected from those crystalline molecular sieves having the MFS structure.

5. The process as claimed in claim 1, wherein the crystalline molecular sieve is selected from those crystalline molecular sieves having the TON structure.

6. The process as claimed in claim 1, wherein the crystalline molecular sieve is a mixture of crystalline molecular sieves having the MFS structure with crystalline molecular sieves having the TON structure.

7. The process of claim 1, including the step of obtaining an alcohol and esterifying said alcohol with an acid selected from the group consisting of inorganic and organic acids.

8. The process of claim 7, wherein said acid is selected from organic acids.

9. The process of claim 7, wherein said acid is selected from polycarboxylic acids.

\* \* \* \* \*

TABLE 2

| Compound, content ppm (expressed as ppm by volume) | Initial Conversion % | Conversion After Days Onstream, % | | | | Nonene Selectivity % | Desorption Temp ° C. |
|---|---|---|---|---|---|---|---|
| | | 1 | 2 | 4 | 5 | | |
| <0.1 | 95 | 93 | 90 | | 87 | 75 | — |
| Isopropyl Sulphide, 2 | 93 | 92 | 90 | | 85 | 75 | 145 |
| Thiophene 2 | 95 | 93 | 91 | | 88 | 75 | |
| Ethylsulphide 7, thiophene 5, tetrahydro thiophene 2 | 95 | 88 | 41 | | 3 | 60 | |
| Dimethyldisulphide 2 | 95 | 72 | | | 5 | 65 | 180 |
| diethylsulphide 7 | 94 | 100 | | | 4 | 64 | >210 |
| Approximation to commercial feed | 95 | 58 | 5 | | | 59 | |
| Tetrahydrothiophene 2 | 95 | 90 | 85 | | 33 | 47 | 180 |
| Dimethyl Sulphide 2 | 92 | 91 | | 41 | | 61 | 195 |
| n-propylthiol | 94 | 90 | 84 | 70 | | 72 | 160 |
| isopropylthiol 2 | 98 | 94 | 90 | | 83 | 76 | 160 |
| COS 5 | 90 | 91 | 88 | 81 | | 73 | 170 |